(12) United States Patent
Nadanami et al.

(10) Patent No.: US 6,797,151 B2
(45) Date of Patent: Sep. 28, 2004

(54) CO SENSOR AND METHOD OF MEASURING CO CONCENTRATION

(75) Inventors: Norihiko Nadanami, Aichi (JP); Tomonori Kondo, Aichi (JP); Ryuji Inoue, Gifu (JP); Noboru Ishida, Gifu (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 100 days.

(21) Appl. No.: 10/035,248

(22) Filed: Jan. 4, 2002

(65) Prior Publication Data

US 2002/0092780 A1 Jul. 18, 2002

(30) Foreign Application Priority Data

Jan. 5, 2001 (JP) .................................... 2001-000734

(51) Int. Cl.[7] .............................................. G01N 27/407
(52) U.S. Cl. ..................... 205/784; 205/785.5; 204/425; 204/426
(58) Field of Search ............................... 204/421–429; 205/784, 785.5

(56) References Cited

U.S. PATENT DOCUMENTS

| 5,302,274 | A | * | 4/1994 | Tomantschger et al. |
| 5,879,525 | A | * | 3/1999 | Kato et al. |
| 5,897,766 | A | | 4/1999 | Kawatsu |
| 6,238,535 | B1 | * | 5/2001 | Taniguchi et al. |

FOREIGN PATENT DOCUMENTS

JP        8-327590        12/1996

* cited by examiner

Primary Examiner—Kaj K. Olsen
(74) Attorney, Agent, or Firm—Sughrue Mion, PLLC

(57) ABSTRACT

A CO sensor and a CO-concentration measurement method which enables accurate measurement of CO concentration irrespective of the hydrogen concentration of a gas under measurement. By applying a first predetermined voltage between first and second electrodes 7 and 8, hydrogen contained in a gas under measurement which has been introduced into a first measurement space 2 via a first diffusion-controlling section 1 dissociates, decomposes, or reacts with another element to generate protons. The thus-generated protons are transported from the first electrode 7 to the second electrode 8 via a first proton-conductive layer 5 or protons are transported from the second electrode 8 to the first electrode 7 via the first proton-conductive layer 5 (when the hydrogen concentration of the measurement gas is extremely low), so that the hydrogen concentration within the first measurement space 2 is controlled to a constant level. The gas under measurement having a controlled hydrogen concentration is introduced into a second measurement space 4 via a second diffusion-controlling section 3, and a second predetermined voltage is applied between third and fourth electrodes 9 and 10. The CO concentration of the gas under measurement is obtained based on current (a limiting proton current) which flows between the third and fourth electrodes 9 and 10. Alternatively, the CO concentration of the gas under measurement is obtained from electromotive force generated between the third and fourth electrodes 9 and 10.

21 Claims, 6 Drawing Sheets

CO SENSOR AND METHOD OF MEASURING CO CONCENTRATION

BACKGROUND OF THE INVENTION

1. Field of the Invention

The present invention relates to a CO sensor and a method of measuring CO concentration, and more particularly to a CO sensor and a method adapted for measuring CO concentration of fuel gas in a fuel cell.

2. Description of the Related Art

In view of worldwide environmental considerations, in recent years active studies have been conducted on fuel cells which serve as a highly-efficient, clean power source. Among them, solid polymer electrolyte fuel cells (PEFCs) are expected to find use as a fuel cell for automobiles, because of their low-temperature operation and high output density. In this case, a reformed gas such as methanol shows promise as a fuel gas. Since CO is generated during a reformation reaction process, depending on conditions such as temperature and pressure, a resultant reformed gas contains CO. Since CO poisons fuel-electrode catalysts, such as Pt of a fuel cell, a CO sensor is needed which can directly detect CO concentration in the reformed gas. Further, such sensor must be able to measure CO concentration in a hydrogen-rich atmosphere.

In view of the foregoing, Japanese Patent Application Laid-Open (kokai) No. 8-327590, proposes a carbon-monoxide detection apparatus (CO sensor) capable of effecting measurement in a hydrogen-rich gas. The proposed carbon-monoxide detection apparatus includes an electrolytic film and two electrodes sandwiching the electrolytic film. A gas to be measured (hereinafter referred to as a "gas under measurement") contacts one electrode; atmospheric air contacts the other electrode; and the CO concentration of the gas is obtained from a potential difference between the two electrodes, to which a predetermined load is connected.

3. Problems Solved by the Invention

In the apparatus disclosed in Japanese Patent Application Laid-Open No. 8-327590, CO concentration is obtained from a difference in potential between two electrodes sandwiching a proton-conductive electrolytic film. However, theoretically, the potentials vary with the hydrogen concentration of a gas under measurement. Therefore, variations in the hydrogen concentration make accurate measurement of CO concentration difficult.

SUMMARY OF THE INVENTION

It is therefore an object of the present invention to provide a CO sensor and a method of measuring CO concentration which enables accurate measurement of CO concentration irrespective of variations in hydrogen concentration of a gas under measurement.

The above-described problem of the prior art have been solved by providing a CO sensor comprising a first measurement space in communication with a measurement gas atmosphere via a first diffusion-controlling section, a second measurement space in communication with the first measurement space via a second diffusion-controlling section, a first proton-conductive layer, a second proton-conductive layer, a first electrode disposed in contact with the first proton-conductive layer and located within the first measurement space, a second electrode disposed in contact with the first proton-conductive layer and located outside the first measurement space, a third electrode disposed in contact with the second proton-conductive layer and located within the second measurement space, a fourth electrode disposed in contact with the second proton-conductive layer and located outside the second measurement space, and a support for supporting the first diffusion-controlling section, the first measurement space, the second diffusion-controlling section, the second measurement space, the first proton-conductive layer, the second proton-conductive layer, the first electrode, the second electrode, the third electrode, and the fourth electrode.

A gas under measurement is introduced into the first measurement space via the first diffusion-controlling section. By applying a first predetermined voltage between the first electrode and the second electrode, hydrogen within the first measurement space dissociates, decomposes, or reacts with another element to thereby generate protons. The thus-generated protons are transported between the first electrode and the second electrode via the first proton-conductive layer, so that the hydrogen concentration within the first measurement space is controlled to a constant level. CO concentration of the gas under measurement is obtained based on an electrical signal which is generated between the third and fourth electrodes upon introduction of the gas under measurement having a controlled hydrogen concentration from the first measurement space to the second measurement space via the second diffusion-controlling section.

In the above-described CO sensor, the electrical signal may be current which flows between the third and fourth electrodes upon application of a second predetermined voltage to the third and fourth electrodes, or electromotive force generated between the third and fourth electrodes.

In one aspect, the present invention is characterized in that a gas is prepared which is the gas under measurement containing CO and adjusted to have a constant hydrogen concentration, hydrogen gas generated by reaction of CO contained in the gas with a hydrogen-containing substance is decomposed or dissociated to thereby generate protons; and the CO concentration of the gas under measurement is obtained based on a limiting proton current which flows by transporting the generated protons through a proton-conductive layer.

The present invention also provides a CO-concentration measurement method which comprises introducing a gas under measurement into a first measurement space via a first diffusion-controlling section, and controlling hydrogen concentration in the first measurement chamber to a constant level by pumping hydrogen contained in the gas under measurement outside the first measurement space or pumping hydrogen into the first measurement space; introducing into a second diffusion-controlling section the gas under measurement present in the first measurement space and having a controlled hydrogen concentration, and reacting CO contained in the gas under measurement with a hydrogen-containing substance at the second diffusion-controlling section to thereby generate hydrogen; introducing into a second measurement space the gas under measurement present in the second diffusion-controlling section and containing the generated hydrogen; and obtaining a CO concentration of the gas under measurement based on a concentration or amount of hydrogen in the second measurement space.

The present invention also provides a CO-concentration measurement method which comprises introducing a gas under measurement into a first measurement space via a first diffusion-controlling section, and controlling hydrogen concentration in the first measurement chamber to a constant level by pumping hydrogen contained in the gas under measurement outside the first measurement space or pumping hydrogen into the first measurement space; introducing into a second measurement space, via a second diffusion-controlling section, the gas under measurement present in the first measurement space and having a controlled hydrogen concentration; reacting CO contained in the gas under measurement with a hydrogen-containing substance at the second measurement space to thereby generate hydrogen; and obtaining a CO concentration of the gas under measurement based on a concentration or amount of hydrogen in the second measurement space.

Next, the measurement principle of the CO sensor and the CO-concentration measurement method according to the present invention will be described.

(1) A gas under measurement is introduced into the first measurement space via the first diffusion-controlling section.

(2) By applying a first predetermined voltage between the first electrode and the second electrode, hydrogen contained in the gas under measurement introduced into the first measurement space dissociates, decomposes, or reacts with another element, whereby hydrogen is pumped outside of the first measurement space in the form of protons. The first predetermined voltage is a voltage which causes dissociation, decomposition, or reaction of hydrogen contained in the gas under measurement and which transports the protons thus generated through the first proton-conductive layer; preferably, a voltage which causes a limiting proton current flow.

(3) The gas under measurement having a controlled hydrogen concentration is introduced into the second diffusion-controlling section.

(4) In the second diffusion-controlling section, CO contained in the gas under measurement having a controlled hydrogen concentration reacts with $H_2O$ as shown in the following formula (1) to thereby generate hydrogen. The reaction of formula 1 may be induced at a location other than the second diffusion-controlling section, e.g., at the second measurement space.

$$CO + H_2O \rightarrow H_2 + CO_2 \qquad \text{formula (1)}$$

(5) The gas under measurement which contains hydrogen generated by the reaction of formula (1) is introduced into the second measurement space.

(6) CO concentration is obtained by measuring the concentration or amount of hydrogen contained in the gas under measurement introduced into the second measurement space. In addition to hydrogen generated by reaction of CO, the measured hydrogen may contain hydrogen which is contained, in a controlled amount or at a controlled concentration, in the gas under measurement introduced from the first measurement space to the second diffusion-controlling section.

First Method of Measuring Concentration or Amount of Hydrogen in the Second Measurement Space By applying a second predetermined voltage between the third and fourth electrodes, hydrogen contained in the gas under measurement introduced into the second measurement space dissociates, decomposes, or reacts with another element, whereby hydrogen is pumped outside of the second measurement space in the form of protons. The second predetermined voltage is a voltage for dissociating, decomposing, or reacting hydrogen contained in the gas under measurement introduced into the second measurement space and for establishing a limiting proton current flow.

At this time, current flows between the third and fourth electrodes in proportion to the amount of hydrogen generated by reaction of CO; i.e., the CO concentration of the gas under measurement. Therefore, the CO concentration of the gas under measurement can be measured based on the current flow.

Second Method of Measuring Concentration or Amount of Hydrogen in the Second Measurement Space Electromotive force is generated between the third and fourth electrodes in accordance with the difference between the concentration of hydrogen contained in the gas under measurement introduced into the second measurement space (hydrogen concentration at the third electrode) and the hydrogen concentration at the fourth electrode.

When the hydrogen concentration at the fourth electrode is constant, the electromotive force changes in accordance with the amount of hydrogen generated by reaction of CO; i.e., the CO concentration of the gas under measurement. Therefore, the CO concentration of the gas under measurement can be measured on the basis of the electromotive force.

According to the CO sensor and the CO-concentration measurement method of the present invention, the concentration of hydrogen contained in the gas under measurement introduced into the second measurement space is controlled by pumping out hydrogen contained in the gas under measurement at the first measurement space. Therefore, the current flowing between the third and fourth electrodes or the electromotive force generated between the third and fourth electrodes does not depend on the hydrogen concentration of the gas under measurement and depends solely on the CO concentration. Accordingly, the CO sensor according to the present invention enables measurement of CO concentration without being affected by the hydrogen concentration of the gas under measurement.

Figure 1:
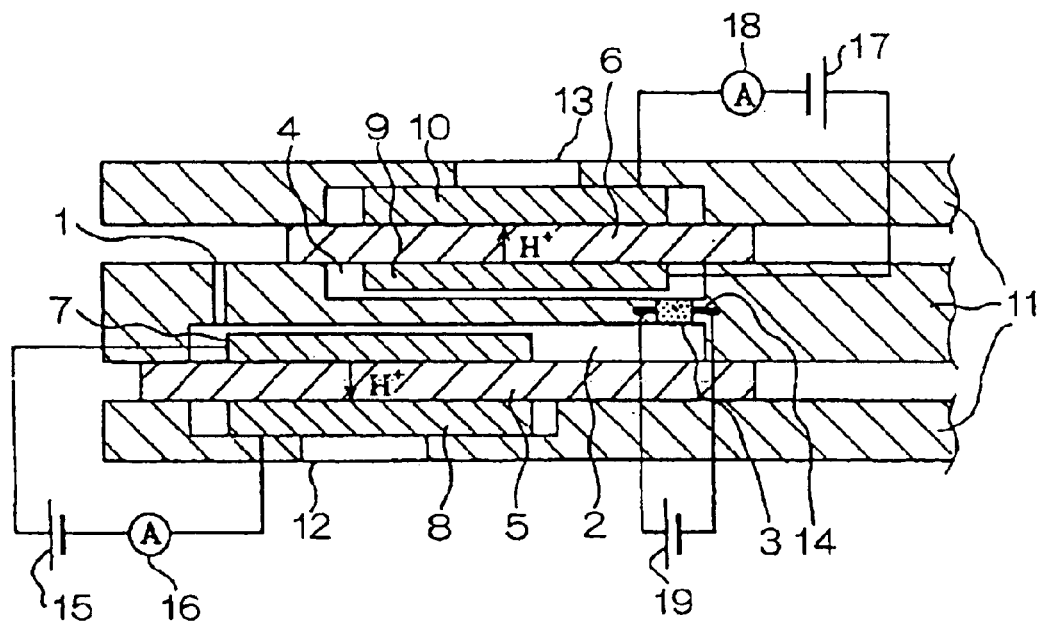
FIG. 1 is a view illustrating a CO sensor according to a first embodiment of the present invention.

DESCRIPTION OF REFERENCE NUMERALS 1 first diffusion-controlling section
2 first measurement space 3 second diffusion-controlling section (filled with catalyst)
4 second measurement space
5 first proton-conductive layer
6 second proton-conductive layer
7 first electrode
8 second electrode
9 third electrode
10 fourth electrode
11 support
12 first opening
13 second opening
14 heater
15 first constant-voltage source
16 first ammeter
17 second constant-voltage source
18 second ammeter
19 heater power source
21 first reference electrode
22 first electrometer
23 control signal indicating potential difference between the first electrode and the first reference electrode
24 first variable-voltage source
25 first ammeter
27 second reference electrode
28 second electrometer
29 control signal indicating potential difference between the third electrode and the second reference electrode
30 second variable-voltage source
31 second ammeter
32 second diffusion-controlling section
33 heater
34 heater power source
35 third electrode
36 fourth electrode
37 third electrometer
40 proton-conductive layer (serving as the first and second proton-conductive layers)
41 heater
42 heater power source

DETAILED DESCRIPTION OF THE PREFERRED EMBODIMENTS

Next, a preferred mode of the present invention will be described. However, the present invention should not be construed us being limited thereto.

A CO sensor according to a preferred mode of the present invention has a first reference electrode disposed in contact with the proton-conductive layer and is located outside the first and second measurement spaces. The first reference electrode allows for changing the voltage applied between the first and second electrodes such that a constant potential difference is produced between the first electrode and the first reference electrode. Therefore, control of hydrogen concentration in the first measurement space can be performed more accurately, even when the resistance between the first and second electrodes varies because of variation in measurement conditions such as temperature.

When the CO concentration is obtained from the current flowing between the third and fourth electrodes, the CO sensor according to a preferred mode of the present invention has a second reference electrode disposed in contact with the proton-conductive layer and located outside the first and second measurement spaces. The second reference electrode allows for changing the voltage applied between the third and fourth electrodes such that a constant potential difference is produced between the third electrode and the second reference electrode. Therefore, the CO concentration can be measured more accurately on the basis of the current flowing between the third and fourth electrodes, even when the resistance between the third and fourth electrodes varies because of variation in measurement conditions such as temperature.

In the CO sensor according to a preferred mode of the present invention, CO contained in the gas under measurement having a controlled hydrogen concentration reacts with a hydrogen-containing substance at the second diffusion-controlling section or the second measurement space.

In the CO sensor according to a preferred mode of the present invention, the second diffusion-controlling section is filled with a catalyst. Preferably, a heater is provided for heating the catalyst filling the second diffusion-controlling section. The catalyst filling the second diffusion-controlling section promotes the reaction represented by the above formula (1). As a result, CO concentration measurement can be performed more accurately. The heater for heating the catalyst further promotes the reaction of formula (1).

In the CO sensor according to a preferred mode of the present invention, a heater is provided for heating the third electrode. The heater for heating the third electrode enables the reaction of formula (1) to proceed effectively at the third electrode, and without the need for providing a catalyst in the second diffusion-controlling section.

In the CO sensor according to a preferred mode of the present invention, the proton-conductive layer is formed of film of a fluorine-containing ion-exchange resin such as perfluorosulfonic acid resin.

The present invention will now be described with reference to the drawings in order to explain in further detail the above-described preferred mode of the present invention. However, the present invention should not be construed as being limited thereto.

First Embodiment:

A first embodiment of the present invention will be described. FIG. 1 is a sectional view showing the configuration of a CO sensor according to the first embodiment of the present invention.

As shown in FIG. 1, the CO sensor according to the first embodiment of the present invention includes a first measurement space 2 communicating with a measurement gas atmosphere via a first diffusion-controlling section 1; a second measurement space 4 communicating with the first measurement space 2 via a second diffusion-controlling section 3 filled with a catalyst; a first proton-conductive layer 5; a second proton-conductive layer 6; a first electrode 7 disposed in contact with the first proton-conductive layer 5 and located within the first measurement space 2; a second electrode 8 disposed in contact with the first proton-conductive layer 5 and located outside the first measurement space 2; a third electrode 9 disposed in contact with the second proton-conductive layer 6 and located within the second measurement space 4; a fourth electrode 10 disposed in contact with the second proton-conductive layer 6 and located outside the second measurement space 4; a heater 14 for heating the second diffusion-controlling section; and a support 11 for supporting the first diffusion-controlling section 1, the first measurement space 2, the second diffusion-controlling section 3, the second measurement space 4, the first proton-conductive layer 5, the second proton-conductive layer 6, the first electrode 7, the second electrode 8, the third electrode 9, the fourth electrode 10, and the heater 14. In the present embodiment, the support is composed of three layers.

Next, the element structure of the CO sensor will be described in detail. At the upper side of the support 11, the second proton-conductive layer 6 and the second layer of the support 11 define the second measurement space 4; and at the lower side of the support 11, the first proton-conductive layer 5 and the second layer of the support 11 define the first measurement space 2. The first diffusion-controlling section 1 and the second diffusion-controlling section 3 are formed in the second layer of the support 11. The heater 14 is embedded in the second layer of the support 11 so as to surround the second diffusion-controlling section 3. The first electrode 7 and the second electrode 8 face each other while sandwiching the first proton-conductive layer 5. The third electrode 9 and the fourth electrode 10 face each other while sandwiching the second proton-conductive layer 6. A first opening 12 is formed in the third layer of the support 11; and a second opening 13 is formed in the first layer of the support 11. The first opening 12 communicates with the second electrode 8 and the measurement gas atmosphere; and the second opening 13 communicates with the fourth electrode 10 and the measurement gas atmosphere. The first and third layers of the support 11 sandwich the second layer of the support 11 to thereby complete the sensor element.

Next, a circuit configuration for controlling the CO sensor will be described. The first electrode 7 and the second electrode 8 are connected via respective lead portions to a circuit including a first constant-voltage source 15 and a first ammeter 16. When a first predetermined voltage is applied between the first electrode 7 and the second electrode 8 by means of the first constant-voltage source 15, current flowing between the first electrode 7 and the second electrode 8 via the first proton-conductive layer 5 can be detected by means of the first ammeter 16. Similarly, the third electrode 9 and the fourth electrode are connected via respective lead portions to a circuit including a second constant-voltage source 17 and a second ammeter 18. When a second predetermined voltage is applied between the third electrode 9 and the fourth electrode 10 by means of the second constant-voltage source 17, current flowing between the third electrode 9 and the fourth electrode 10 via the second proton-conductive layer 6 can be detected by means of the second ammeter 18. Further, the heater 14 is connected to a heater power source 19 via lead portions.

Each of the proton-conductive layers is formed of a material suitable for operation (proton conduction) at relatively low temperatures; e.g., NAFION (trademark of Du Pont), which is a fluorine-containing ion-exchange resin film.

Each of the electrodes is formed of a porous material such as porous carbon and carries a catalyst such as Pt on a side contacting the corresponding proton-conductive layer.

The layers of the support are formed of an insulating material; e.g., resin or ceramic such as alumina.

The diffusion-controlling sections may be formed of porous alumina ceramic having continuous pores, or may be in the form of a very small diameter hole. The second diffusion-controlling section 3 may be filled with a catalyst which is carried on a porous carrier such as porous carbon or alumina, or filled with a catalyst powder.

Physical contact between the electrodes and the corresponding proton-conductive layers may be established by sandwiching the electrodes and the proton-conductive layers between the layers of the support, or by bonding the electrodes to the corresponding proton-conductive layers by hot-pressing.

A method of measuring CO concentration using the above-described CO sensor will now be described. By applying the first predetermined voltage between the first electrode 7 and the second electrode 8, hydrogen contained in a gas under measurement which has been introduced into the first measurement space 2 via the first diffusion-controlling section 1 is dissociated, decomposed, or reacted with another element to generate protons.

The thus-generated protons are transported from the first electrode 7 to the second electrode 8 via the first proton-conductive layer 5, or protons are transported from the second electrode 8 to the first electrode 7 via the first proton-conductive layer 5 (when the hydrogen concentration of the measurement gas is extremely low), so that the hydrogen concentration within the first measurement space 2 is controlled to a constant level. CO contained in the gas under measurement having a controlled hydrogen concentration reacts with $H_2O$ in the second diffusion-controlling section 3 in order to produce hydrogen. The gas under measurement containing the thus-generated hydrogen is introduced into the second measurement space 4. By applying the second predetermined voltage between the third electrode 9 and the fourth electrode 10, current (a limiting proton current) flows between the third electrode 9 and the fourth electrode 10. On the basis of the current (limiting proton current), a CO concentration of the gas under measurement is obtained.

Second Embodiment:

Next, a second embodiment of the present invention will be described. A CO sensor according to the second embodiment of the present invention has a first reference electrode. In order to avoid repeated descriptions, the structural and functional features of the CO sensor according to the second embodiment which are similar to those of the CO sensor according to the first embodiment will not be described, and when necessary reference will be made to the description of the first embodiment. The elements of the CO sensor according to the second embodiment which have configurations or functions similar to those of the CO sensor according to the first embodiment will be denoted by the same reference numerals. Detailed description will mainly be provided of features that differ from those of the first embodiment.

Figure 2:
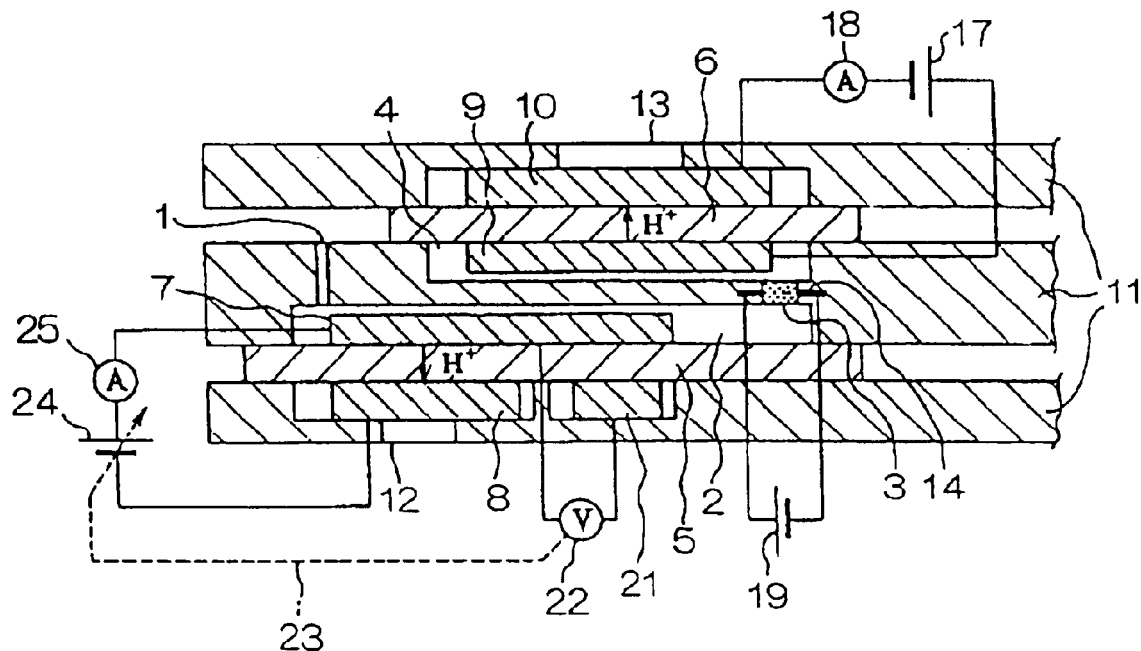
FIG. 2 is a view illustrating a CO sensor according to a second embodiment of the present invention.

FIG. 2 is a sectional view showing the configuration of a CO sensor according to the second embodiment of the present invention. As shown in FIG. 2, the CO sensor according to the second embodiment has a first reference electrode 21. Specifically, the first reference electrode 21 is provided in contact with the first proton-conductive layer 5 and is located outside of the first measurement space 2 and the second measurement space 4. The function of the first reference electrode 21 is to reduce the influence of variation in hydrogen concentration of a gas under measurement.

The first electrode 7, the second electrode 8, and the first reference electrode 21 are connected via respective lead portions to a circuit including a first electrometer 22, a first variable-voltage source 24, and a first ammeter 25. A sufficiently high voltage (first predetermined voltage) is applied between the first electrode 7 and the second electrode 8 by means of the first variable-voltage source 24, such that a potential difference between the first electrode 7 and the first reference electrode 21, which can be measured by the first electrometer 22, assumes a constant value. Reference numeral 23 denotes a control signal indicating the potential difference between the first electrode 7 and the first reference electrode 21. Current which flows between the first electrode 7 and the second electrode 8 as a result of application of the first predetermined voltage is measured by means of the first ammeter 25.

In order to stabilize hydrogen concentration in the vicinity of the first reference electrode 21, the first reference electrode 21 is preferably a self-generation-type reference electrode, which can be implemented as follows. A very small constant current is passed from the first electrode 7 to the first reference electrode 21 (protons are transported from the first electrode 7 to the first reference electrode 21 via the first proton conductive layer 5) in order to generate hydrogen gas in the vicinity of the first reference electrode 21, and a portion of the thus-generated hydrogen gas is leaked to the outside via a leak resisting portion (e.g., a very small diameter hole) of predetermined size formed in the support 11.

In the above-described CO sensor, the voltage applied between the first electrode 7 and the second electrode 8 can be changed based on the potential difference between the first electrode 7 and the first reference electrode 21. Therefore, voltage applied between the first electrode 7 and the second electrode 8 can be controlled optimally so that a higher voltage is applied when the resistance between the first electrode 7 and the second electrode 8 increases due to variation in the temperature of the gas under measurement or the temperature of the element itself, and a lower voltage is applied when the resistance between the first electrode 7 and the second electrode 8 decreases. Since the hydrogen concentration on the first electrode 7 can be controlled to a constant level by maintaining the potential difference between the first electrode 7 and the first reference electrode 21 constant, the hydrogen concentration in the first measurement space 2 can be controlled more accurately.

Third Embodiment:

A third embodiment of the present invention will now be described. A CO sensor according to the third embodiment of the present invention has a second reference electrode. In order to avoid repeated descriptions, the structural and functional features of the CO sensor according to the third embodiment which are similar to those of the CO sensor according to the second embodiment will not be described, and when necessary reference will be made to the description of the second embodiment. The elements of the CO sensor according to the third embodiment which have configurations or functions similar to those of the CO sensor according to the second embodiment will be denoted by the same reference numerals. Detailed description will mainly be provided of features that differ from those of the second embodiment.

Figure 3:
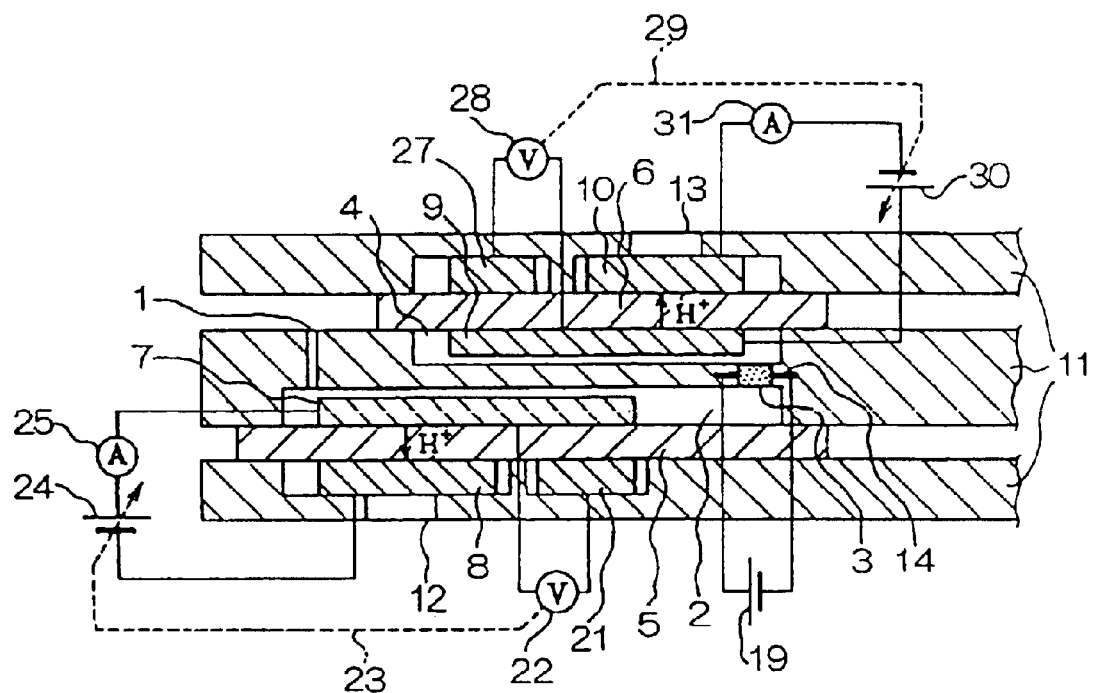
FIG. 3 is a view illustrating a CO sensor according to a third embodiment of the present invention.

FIG. 3 is a sectional view showing the configuration of a CO sensor according to the third embodiment of the present invention. As shown in FIG. 3, the CO sensor according to the third embodiment has a second reference electrode 27, as well as the first reference electrode 21. Specifically, the second reference electrode 27 is provided so as to contact the second proton-conductive layer 6 and is located outside of the first measurement space 2 and the second measurement space 4. The function of the second reference electrode 27 is to reduce the influence of variation in hydrogen concentration of a gas under measurement.

The third electrode 9, the fourth electrode 10, and the second reference electrode 27 are connected via respective lead portions to a circuit including a second electrometer 28, a second variable-voltage source 30, and a second ammeter 31. A sufficiently high voltage (second predetermined voltage) is applied between the third electrode 9 and the fourth electrode 10 by means of the second variable-voltage source 30, such that a potential difference between the third electrode 9 and the second reference electrode 27, which can be measured by the second electrometer 28, assumes a constant value. Reference numeral 29 denotes a control signal indicating the potential difference between the third electrode 9 and the second reference electrode 27. Current which flows between the third electrode 9 and the fourth electrode 10 due to application of the second predetermined voltage is measured by means of the second ammeter 31.

In order to stabilize hydrogen concentration in the vicinity of the second reference electrode 27, the second reference electrode 27 is preferably a self-generation-type reference electrode, which can be implemented as follows. A very small constant current is passed from the third electrode 9 to the second reference electrode 27 (protons are transported from the third electrode 9 to the second reference electrode 27 via the second proton conductive layer 6) in order to generate hydrogen gas in the vicinity of the second reference electrode 27, and a portion of the thus-generated hydrogen gas is leaked to the outside via a leak resisting portion (e.g., a very small diameter hole) of predetermined size formed in the support 11.

In the above-described CO sensor, the voltage applied between the third electrode 9 and the fourth electrode 10 can be changed based on the potential difference between the third electrode 9 and the second reference electrode 27. Therefore, the voltage applied between the third electrode 9 and the fourth electrode 10 can be controlled optimally so that a higher voltage is applied when the resistance between the third electrode 9 and the fourth electrode 10 increases due to variation in the temperature of the gas under measurement or the temperature of the element itself, and a lower voltage is applied when the resistance between the resistance between the third electrode 9 and the fourth electrode 10 decreases. Since the hydrogen concentration on the third electrode 9 can be controlled to a constant level by maintaining the potential difference between the third electrode 9 and the second reference electrode 27 constant, CO concentration can be measured more accurately based on the current flowing through the third electrode 9 and the fourth electrode 10.

Figure 4:
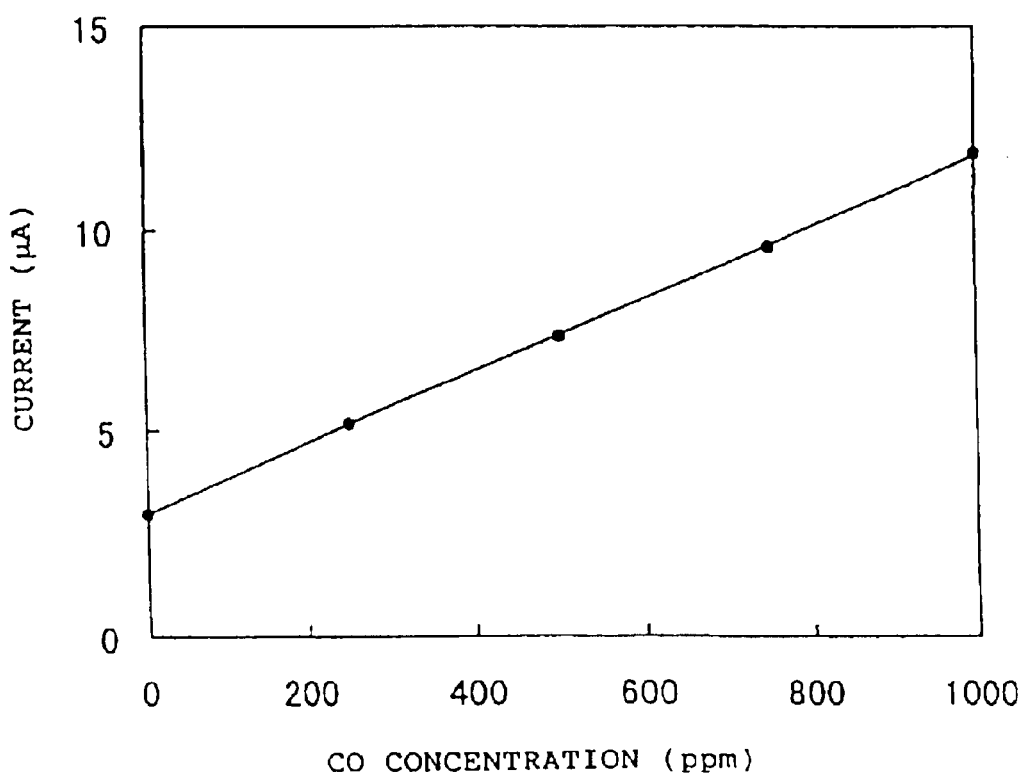
FIG. 4 is a graph of the results of Measurement Example 1 performed using the CO sensor according to the third embodiment of the present invention.

Measurement Example 1:

CO concentration was measured using the CO sensor according to the third embodiment. FIG. 4 is a graph showing the measurement results (Measurement Example 1). In FIG. 4, the vertical axis represents current flowing between the third and fourth electrodes, and the horizontal axis represents CO concentration of a gas under measurement (true value). In this measurement, the voltage sources were controlled such that a potential difference of 200 mV was generated between the first electrode and the first reference electrode and between the third electrode and the second reference electrode. Further, a very small constant current was caused to flow from the first electrode to the first reference electrode and from the third electrode to the second reference electrode so that the first and second reference electrodes operated as self-generation-type reference electrodes. Further, the second diffusion-controlling section was heated by the heater to 120° C. Other measurement conditions are shown below.

Measurement Conditions of Measurement Example 1, Dimensions and Materials of CO Sensor:

(Materials)

Proton-conductive layers: Film of NAFION (trade name of Du Pont)

Electrodes: Carbon paper having a surface coated with Pt-carrying carbon powder

Support: Alumina ceramic substrate having lead portions, a heater, and first and second diffusion-controlling sections formed on the surface thereof or inside the substrate.

Component of catalyst charged into the second diffusion-controlling section: Pt (Dimensions)
Length: 40 mm, Thickness: 6 mm, Width: 7 mm (element portion)
(Fabrication Method)
(1) Bonding of proton-conductive layers and electrodes
Electrodes formed of carbon paper having a surface coated with Pt-carrying carbon powder, were bonded to a NAFION film by means of hot-pressing.
(2) Method of fabricating support
Metal paste containing Pt as a predominant component was screen printed onto an alumina green sheet to form lead portions and a heater portion thereon.
Portions of the green sheet were punched to obtain a plurality of green sheets having predetermined shapes, respectively, which were then stacked, bonded together by applying pressure, and fired.
Diffusion-controlling sections were formed by punching portions of the formed sheet, or by means of laser machining or the like performed after the firing step.
The catalyst of the second Diffusion-controlling section was charged into a hole formed in the green sheet and serving as the second diffusion-controlling section, and then fired integrally, or charged into the hole after firing.
(Components, Temperature, etc. of Gas under Measurement)
Gas composition: CO=0–1000 ppm, $H_2$=50%, $CO_2$=15%, $H_2O$=25%, $N_2$=balance
Gas temperature: 80° C.
Gas flow rate: 10 L/min As shown in FIG. 4, the current flowing between the third and fourth electrodes changes linearly with an increase in CO concentration. Therefore, the CO sensor of the present invention enables accurate measurement of CO concentration.

Fourth Embodiment:

A fourth embodiment of the present invention will now be described. A CO sensor according to the fourth embodiment of the present invention has a heater for heating the third electrode. In order to avoid repeated descriptions, the structural and functional features of the CO sensor according to the fourth embodiment which are similar to those of the CO sensor according to the first embodiment will not be described, and when necessary reference will be made to the description of the first embodiment. The elements of the CO sensor according to the fourth embodiment which have configurations or functions similar to those of the CO sensor according to the first embodiment will be denoted by the same reference numerals. Detailed description will mainly be provided of features that differ from those of the first embodiment.

Figure 5:
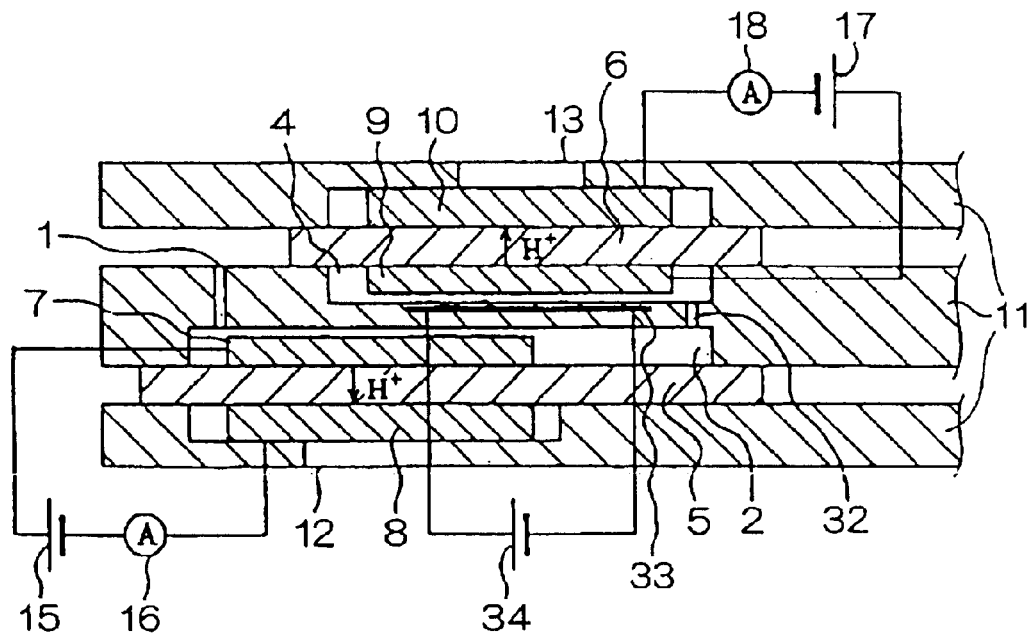
FIG. 5 is a view illustrating a CO sensor according to a fourth embodiment of the present invention.

FIG. 5 is a sectional view showing the configuration of a CO sensor according to a fourth embodiment of the present invention. As shown in FIG. 5, the CO sensor according to the fourth embodiment has an empty through-hole serving as a second diffusion-controlling section 32, and a heater 33 which is embedded in the second layer of the support 11 in the vicinity of the third electrode 9 in order to heat the third electrode 9 (the heater 33 is disposed on the upper side of the second layer of the support 11, on which side the second measurement space 4 is formed). Electrical power is supplied from a heater power source 34 to the heater 33.

Since the third electrode 9 is heated by the heater 33, the action of the catalyst carried on the third electrode 9 is enhanced to thereby promote the reaction of formula (1).

Fifth Embodiment:

A fifth embodiment of the present invention will now be described. A CO sensor according to the fifth embodiment of the present invention has a first reference electrode (see the second embodiment) and a heater for heating the third electrode (see the fourth embodiment). In order to avoid repeated descriptions, the structural and functional features of the CO sensor according to the fifth embodiment which are similar to those of the CO sensors according to the second and fourth embodiments will not be described, and reference will be made to the descriptions of the second and fourth embodiments as needed. The elements of the CO sensor according to the fifth embodiment which have configurations or functions similar to those of the CO sensors according to the second and fourth embodiments will be denoted by the same reference numerals. Detailed description will mainly be provided of features that are different from those of the second and fourth embodiments.

Figure 6:
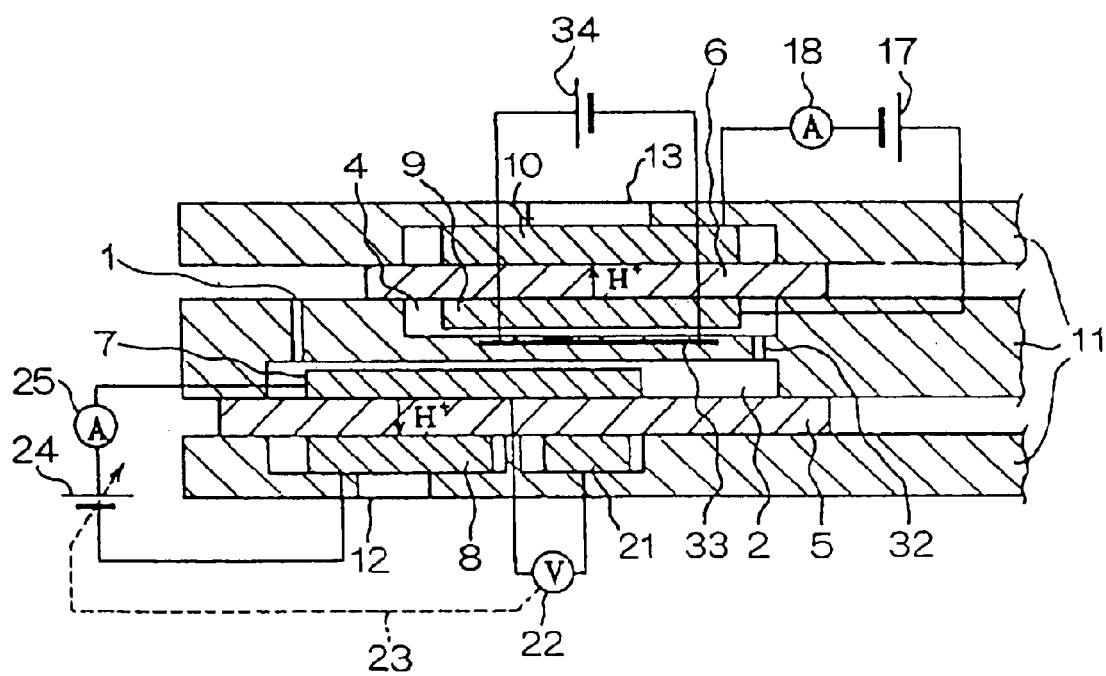
FIG. 6 is a view illustrating a CO sensor according to a fifth embodiment of the present invention.

FIG. 6 is a sectional view showing the configuration of a CO sensor according to the fifth embodiment of the present invention. As shown in FIG. 6, the CO sensor according to the fifth embodiment has an empty through-hole serving as a second diffusion-controlling section 32, and a heater 33 which is embedded in the second layer of the support 11 in the vicinity of the third electrode 9 in order to heat the third electrode 9 (the heater 33 is disposed on the upper side of the second layer of the support 11, on which side the second measurement space 4 is formed). Moreover, the CO sensor has a first reference electrode 21 which is disposed in contact with the first proton-conductive layer 5 and is located outside of the first measurement space 2 and the second measurement space 4. The first reference electrode 21 is formed to reduce influence of variation in hydrogen concentration of a gas under measurement.

Figure 7:
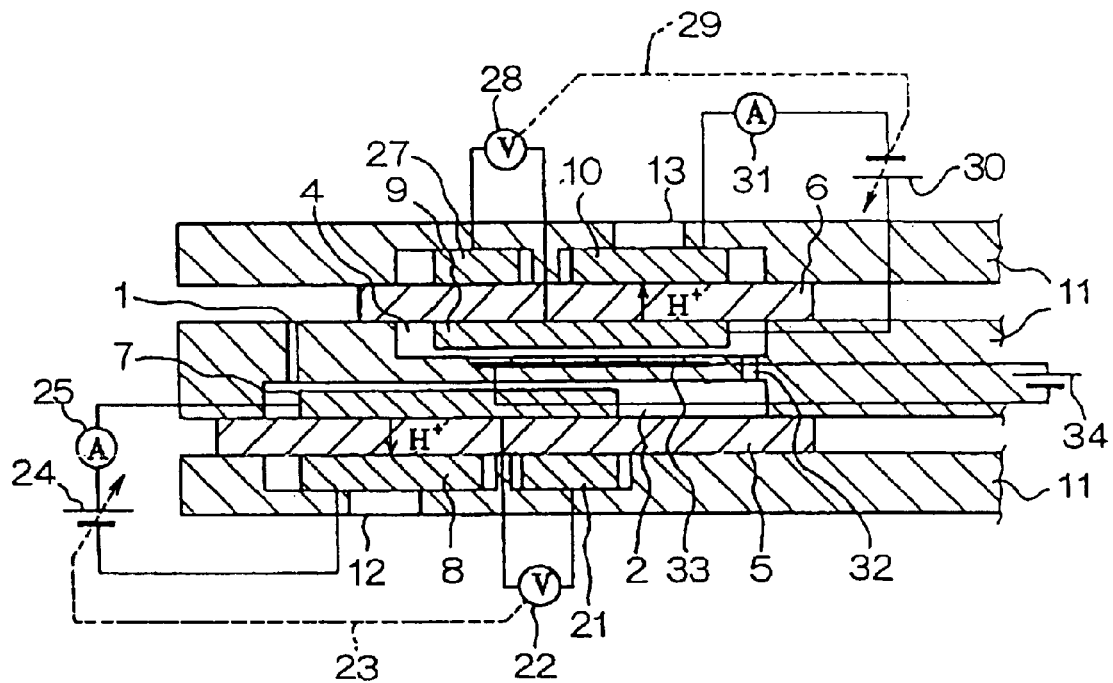
FIG. 7 is a view illustrating a CO sensor according to a sixth embodiment of the present invention.

Sixth Embodiment:

A sixth embodiment of the present invention will now be described. FIG. 7 is a sectional view showing the configuration of a CO sensor according to the sixth embodiment of the present invention. As shown in FIG. 7, the CO sensor according to the sixth embodiment has a first reference electrode 21 (see the second embodiment), a second reference electrode 27 (see the third embodiment), and a heater 33 for heating the third electrode 9 (see the fourth embodiment). These configurations and functions are clearly shown in the descriptions of the second, third, and fourth embodiments.

Seventh Embodiment:

A seventh embodiment of the present invention will now be described. In the CO sensor according to the seventh embodiment of the present invention, CO concentration is obtained from electromotive force generated between the third and fourth electrodes (CO sensors according to eight to tenth embodiments are of the same type). In order to avoid repeated descriptions, the structural and functional features of the CO sensor according to the seventh embodiment which are similar to those of the CO sensor according to the first embodiment will not be described, and reference will be made to the description of the first embodiment as needed. The elements of the CO sensor according to the seventh embodiment which have configurations or functions similar to those of the CO sensor according to the first embodiment will be denoted by the same reference numerals. Detailed description will mainly be provided of features that differ from those of the first embodiment.

Figure 8:
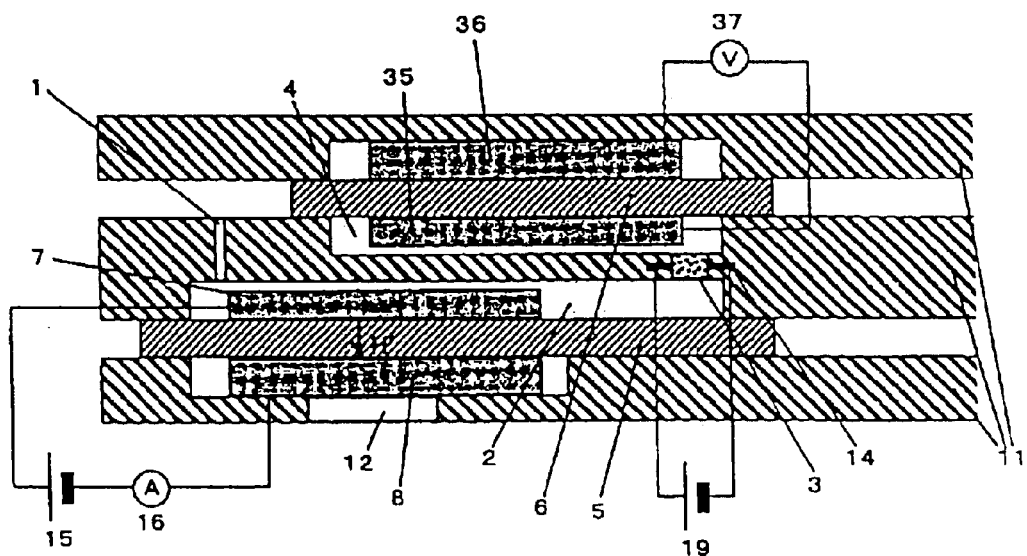
FIG. 8 is a view illustrating a CO sensor according to a seventh embodiment of the present invention.

FIG. 8 is a sectional view showing the configuration of a CO sensor according to the seventh embodiment of the present invention. As shown in FIG. 8, the CO sensor according to the seventh embodiment has a fourth electrode 36 which reduces the influence of variation in hydrogen concentration of a gas under measurement.

A third electrode 35 and the fourth electrode 36 are connected to third electrometer 37 via respective lead portions in order to measure electromotive force generated between the third electrode 35 and the fourth electrode 36 via the second proton-conductive layer 6.

A method of measuring CO concentration using the above-described CO sensor will be described. By applying the first predetermined voltage between the first electrode 7 and the second electrode 8, hydrogen contained in a gas under measurement which has been introduced into the first measurement space 2 via the first diffusion-controlling section 1 is dissociated, decomposed, or reacted with another element in order to generate protons. The thus-generated protons are transported from the first electrode 7 to the second electrode 8 via the first proton-conductive layer 5, or protons are transported from the second electrode 8 to the first electrode 7 via the first proton-conductive layer 5 (when the hydrogen concentration of the measurement gas is extremely low), so that the hydrogen concentration within the first measurement space 2 is controlled to a constant level. CO contained in the gas under measurement having a controlled hydrogen concentration reacts with $H_2O$ in the second diffusion-controlling section 3 to produce hydrogen. The gas under measurement containing the thus-generated hydrogen is introduced to the second measurement space 4. The electromotive force generated between the third electrode 35 and the fourth electrode 36 changes in accordance with the concentration of the generated hydrogen. Therefore, the CO concentration of the gas under measurement can be obtained based on the electromotive force generated between the third electrode 35 and the fourth electrode 36.

Figure 9:
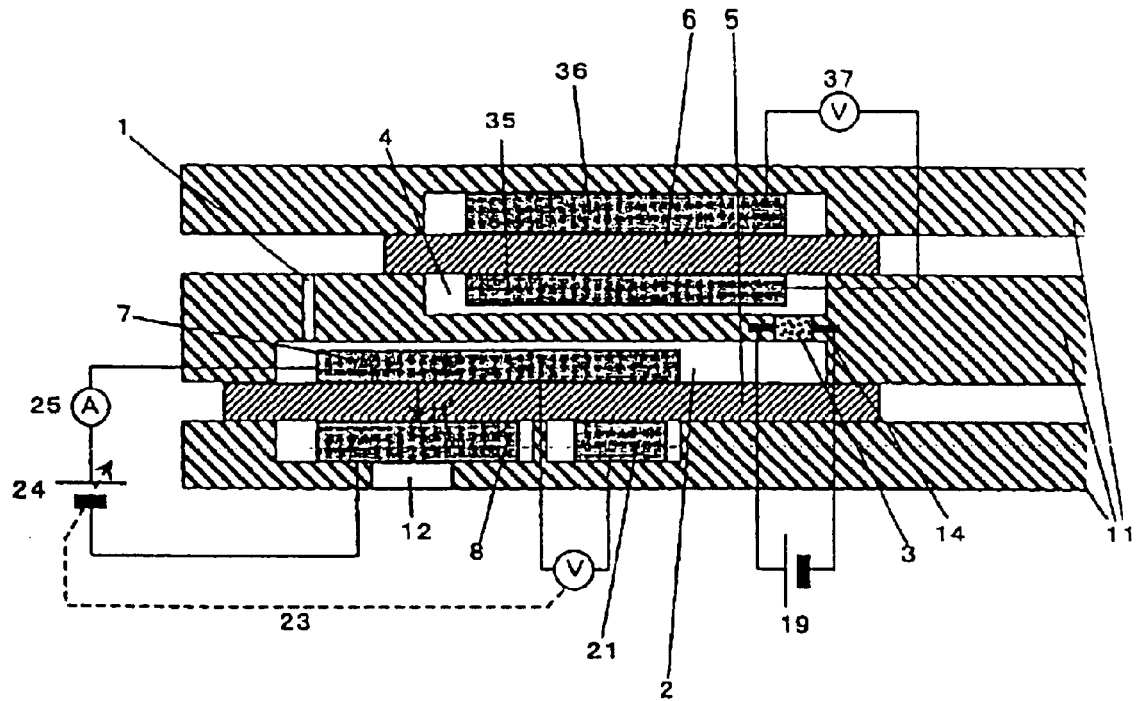
FIG. 9 is a view illustrating a CO sensor according to an eighth embodiment of the present invention.

Eighth Embodiment:

An eighth embodiment of the present invention will now be described. FIG. 9 is a sectional view showing the configuration of a CO sensor according to the eighth embodiment of the present invention. As shown in FIG. 9, the CO sensor according to the eighth embodiment has a first reference electrode (see the second embodiment) in addition to the structural elements of the CO sensor according to the seventh embodiment. The configuration and function of the reference electrode 21 are clearly shown in the description of the second embodiment, and the method of measuring CO concentration using the CO sensor of the eighth embodiment is clearly shown in the description of the seventh embodiment. Therefore, in order to avoid repeated descriptions, reference is made to the descriptions of the second and seventh embodiments.

Figure 10:
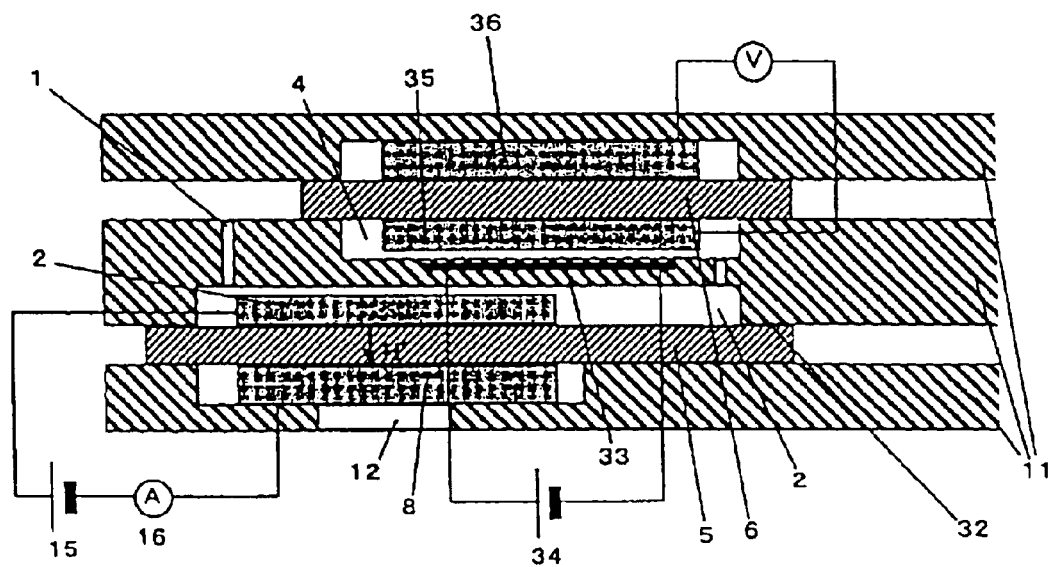
FIG. 10 is a view illustrating a CO sensor according to a ninth embodiment of the present invention.

Ninth Embodiment:

A ninth embodiment of the present invention will be described. FIG. 10 is a sectional view showing the configuration of a CO sensor according to the ninth embodiment of the present invention. As shown in FIG. 10, the CO sensor according to the ninth embodiment differs from the CO sensor according to the seventh embodiment in that the CO sensor of the present embodiment has a heater 33 for heating the third electrode 35 (see the fourth embodiment). The configuration and function of the heater 33 are clearly shown in the description of the fourth embodiment, and the method of measuring CO concentration using the CO sensor according to the eighth embodiment is clearly shown in the description of the seventh embodiment. Therefore, in order to avoid repeated descriptions, reference is made to the descriptions of the fourth and seventh embodiments rather than providing a description of the ninth embodiment.

Figure 11:
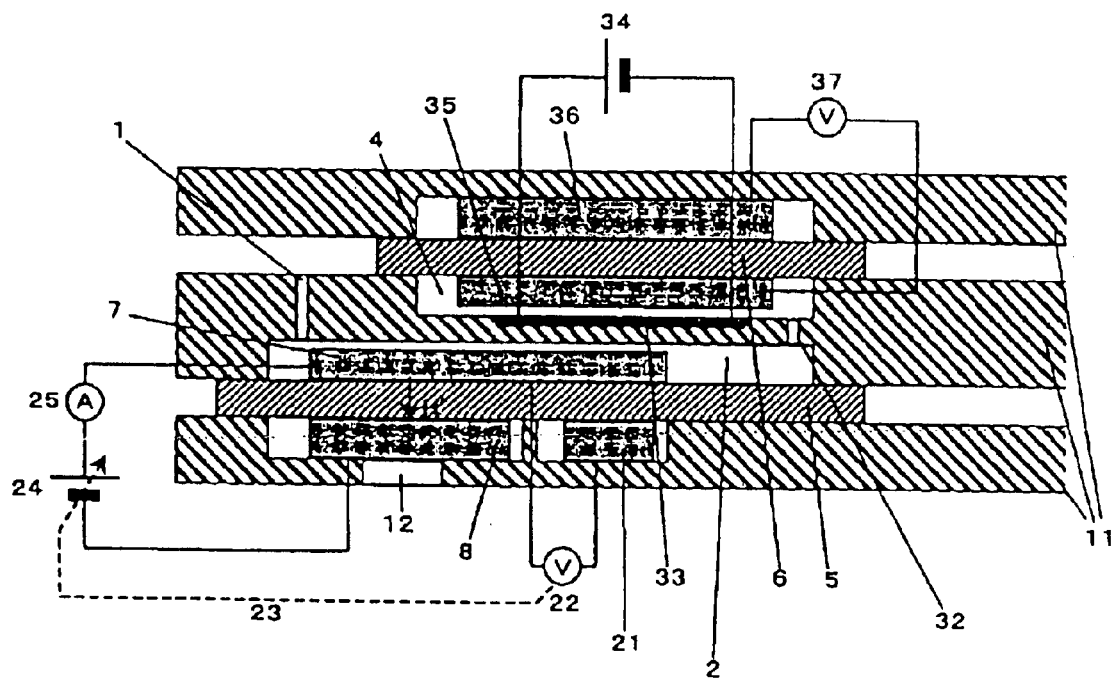
FIG. 11 is a view illustrating a CO sensor according to a tenth embodiment of the present invention.

Tenth Embodiment:

A tenth embodiment of the present invention will now be described. FIG. 11 is a sectional view showing the configuration of a CO sensor according to the tenth embodiment of the present invention. As shown in FIG. 11, the CO sensor according to the tenth embodiment differs from the CO sensor according to the seventh embodiment in that the CO sensor of the present embodiment has a first reference electrode 21 (see the second embodiment) and a heater 33 for heating the third electrode 35 (see the fourth embodiment). The configurations and functions of these additional elements are clearly shown in the descriptions of the second and fourth embodiments, and the method of measuring CO concentration using the CO sensor according to the tenth embodiment is clearly shown in the description of the seventh embodiment. Therefore, in order to avoid repeated descriptions, reference is made to the descriptions of the second, fourth, and seventh embodiments.

Eleventh Embodiment:

An eleventh embodiment of the present invention will be described. The CO sensor according to the eleventh embodiment differs from the CO sensors according to the first through tenth embodiments in that the first and second proton-conductive layers are replaced with a common proton-conductive layer, and measurement spaces, electrodes, etc. are disposed symmetrically. With regard to the configurations and functions of elements of the CO sensor according to the eleventh embodiment which are identical with those of the CO sensors according to the first through tenth embodiments, reference is made to the corresponding portions of the descriptions of the first through tenth embodiments (e.g., with regard to the measurement method, see the first embodiment). Description will mainly be provided of the feature of the CO sensor of the eleventh embodiment which differ from those of the first through tenth embodiments.

Figure 12:
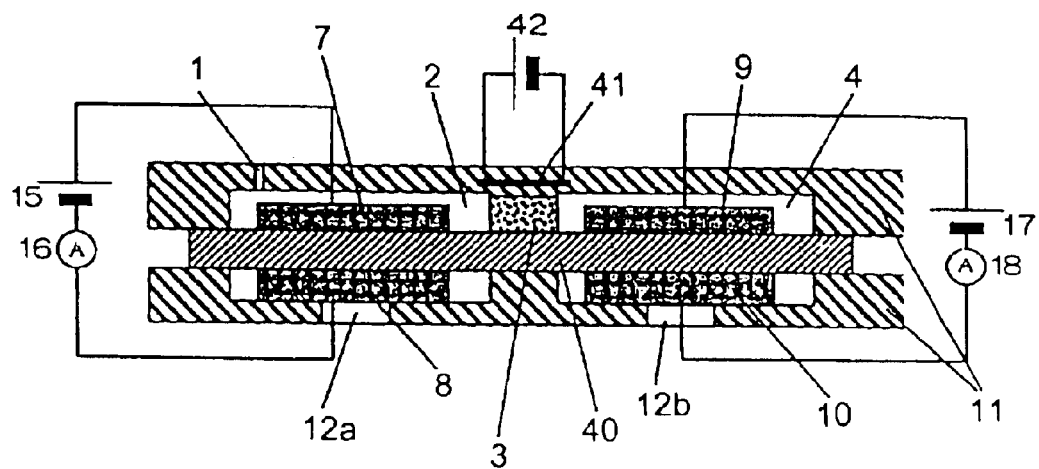
FIG. 12 is a view illustrating a CO sensor according to an eleventh embodiment of the present invention.

FIG. 12 is a sectional view showing the configuration of a CO sensor according to the eleventh embodiment of the present invention. As shown in FIG. 12, a first measurement space 2 is formed within a support 11 located at one side, and a second measurement space 4 is formed within the support 11 located at the other side. The first measurement space 2 communicates with a measurement gas atmosphere via a first diffusion-controlling section 1. The second measurement space 4 communicates with the first measurement space 2 via a second diffusion-controlling section 3. A heater 41 is embedded in the support 11 in the vicinity of the second diffusion-controlling section 3 and receives electrical power from a heater power source 42. Further, a proton-conductive layer 40 is supported within the support 11. First and second electrodes 7 and 8 are disposed at a left-hand portion of the proton-conductive layer 40, and third and fourth electrodes 9 and 10 are disposed at a right-hand portion of the proton-conductive layer 40. The first and second electrodes 7 and 8 face each other via the proton-conductive layer 40; and the third and fourth electrodes 9 and 10 face each other via the proton-conductive layer 40. The second electrode 8 communicates with the outside via an opening 12a; and the fourth electrode 10 communicates with the outside via an opening 12b.

The CO sensor of the eleventh embodiment is configured such that hydrogen gas concentration is measured based on the proton current flowing between the third electrode 9 and the fourth electrode 10. However, the CO sensor of the eleventh embodiment may also be configured such a manner that hydrogen gas concentration is measured based on electromotive force generated between the third electrode 9 and the fourth electrode 10 due to a difference in hydrogen gas concentration.

According to the present invention, a CO sensor and a CO-concentration measurement method are provided which enable accurate measurement of CO concentration even when the hydrogen concentration of a gas under measurement varies.

It should further be apparent to those skilled in the art that various changes in form and detail of the invention as shown and described above may be made. It is intended that such changes be included within the spirit and scope of the claims appended hereto.

This application is based on Japanese Patent Application No. 2001-734 filed Jan. 5, 2001, the disclosure of which is incorporated herein by reference in its entirety.

What is claimed is:

1. A CO sensor which comprises a first measurement space in communication with a measurement gas atmosphere via a first diffusion-controlling section for introducing a gas under measurement into the first measurement space, a second measurement space in communication with the first measurement space via a second diffusion-controlling section, a first electrode disposed in contact with a first proton-conductive layer and located within the first measurement space, a second electrode disposed in contact with the first proton-conductive layer and located outside the first measurement space, a third electrode disposed in contact with a second proton-conductive layer and located within the second measurement space, a fourth electrode disposed in contact with the second proton-conductive layer and located outside the second measurement space, and a support for supporting the first diffusion-controlling section, the first measurement space, the second diffusion-controlling section, the second measurement space, the first proton-conductive layer, the second proton-conductive layer, the first electrode, the second electrode, the third electrode, and the fourth electrode, said CO sensor further comprising:

means for controlling the hydrogen concentration within the first measurement space to a constant level by pumping hydrogen contained in the gas under measurement outside the first measurement space or by pumping hydrogen into the first measurement space upon application of a first predetermined voltage between the first and second electrodes, and means for obtaining a CO concentration of the gas under measurement based on current flowing between the third and fourth electrodes upon introduction of the gas under measurement having a controlled hydrogen concentration from the first measurement space to the second measurement space via the second diffusion-controlling section and application of a second predetermined voltage between the third and fourth electrodes.

2. The CO sensor as claimed in claim 1, further comprising a first reference electrode disposed in contact with the first proton-conductive layer and located outside the first and second measurement spaces, said first predetermined voltage applied between the first and second electrodes producing a constant potential difference between the first electrode and the first reference electrode.

3. The CO sensor as claimed in claim 2, further comprising a second reference electrode disposed in contact with the second proton-conductive layer and located outside the first and second measurement spaces, said second predetermined voltage applied between the third and fourth electrodes producing a constant potential difference between the third electrode and the second reference electrode.

4. The CO sensor as claimed in claim 1, which comprises means for reacting CO contained in the gas under measurement with a hydrogen-containing substance at the second diffusion-controlling section or the second measurement space to generate hydrogen gas.

5. The CO sensor as claimed in claim 1, wherein the second diffusion-controlling section comprises a catalyst for reacting CO contained in the gas under measurement with a hydrogen-containing substance to generate hydrogen gas.

6. The CO sensor as claimed in claim 5, further comprising a heater for heating the catalyst.

7. The CO sensor as claimed in claim 1, further comprising a heater for heating the third electrode.

8. The CO sensor as claimed in claim 1, wherein hydrogen within the first measurement space is dissociated to generate protons, and the thus-generated protons are transported between the first and second electrodes via the first proton-conductive layer such that the hydrogen concentration within the first measurement space is controlled to a constant level.

9. The CO sensor as claimed in claim 1, wherein hydrogen within the second measurement space is dissociated to thereby generate protons by application of said second predetermined voltage between the third and fourth electrodes, and the thus-generated protons are transported through the second proton-conductive layer to establish a limiting proton current flowing between the third and fourth electrodes.

10. A CO sensor which comprises a first measurement space in communication with a measurement gas atmosphere via a first diffusion-controlling section for introducing a gas under measurement into the first measurement space, a second measurement space in communication with the first measurement space via a second diffusion-controlling section, a first electrode disposed in contact with a first proton-conductive layer and located within the first measurement space, a second electrode disposed in contact with the first proton-conductive layer and located outside the first measurement space, a third electrode disposed in contact with a second proton-conductive layer and located within the second measurement space, a fourth electrode disposed in contact with the second proton-conductive layer and located outside the second measurement space, and a support for supporting the first diffusion-controlling section, the first measurement space, the second diffusion-controlling section, the second measurement space, the first proton-conductive layer, the second proton-conductive layer, the first electrode, the second electrode, the third electrode, and the fourth electrode, said CO sensor further comprising:

means for controlling the hydrogen concentration within the first measurement space to a constant level by pumping hydrogen contained in the gas under measurement outside the first measurement space or by pumping hydrogen into the first measurement space upon application of a first predetermined voltage between the first and second electrodes, and means for obtaining a CO concentration of the gas under measurement based on an electromotive force generated between the third and fourth electrodes upon introduction of the gas under measurement having a controlled hydrogen concentration from the first measurement space to the second measurement space via the second diffusion-controlling section.

11. The CO sensor as claimed in claim 10, further comprising a first reference electrode disposed in contact with the first proton-conductive layer and located outside the first and second measurement spaces, said first predetermined voltage applied between the first and second electrodes producing a constant potential difference between the first electrode and the first reference electrode.

12. The CO sensor as claimed in claim 10, which comprises means for reacting CO contained in the gas under measurement with a hydrogen-containing substance at the second diffusion-controlling section or the second measurement space to generate hydrogen gas.

13. The CO sensor as claimed in claim 10, wherein the second diffusion-controlling section comprises a catalyst for reacting CO contained in the gas under measurement with a hydrogen-containing substance to generate hydrogen gas.

14. The CO sensor as claimed in claim 13, further comprising a heater for heating the catalyst.

15. The CO sensor as claimed in claim 10, further comprising a heater for heating the third electrode.

16. The CO sensor as claimed in claim 10, wherein hydrogen within the first measurement space is dissociated to generate protons, and the thus-generated protons are transported between the first and second electrodes via the first proton-conductive layer such that the hydrogen concentration within the first measurement space is controlled to a constant level.

17. A CO sensor for measuring CO concentration of a gas to be measured containing CO and hydrogen, which comprises:
a first measurement space in communication with a measurement gas atmospheric via a first diffusion-controlling section for introducing a gas under measurement into the first measurement space,
a second measurement space in communication with the first measurement space via a second diffusion-controlling section,
means for adjusting the hydrogen concentration of the gas to be measured in the first measurement space to a constant value,
means for reacting CO continued in the adjusted gas with a hydrogen-containing substance to thereby generate hydrogen gas,
means for dissociating the hydrogen gas produced by reaction of CO with the hydrogen-containing substance in the second measurement to thereby generate protons,
means for transporting the protons thus generated through a proton-conductivity layer, and
means for obtaining the CO concentration of the gas under measurement by measuring a limiting proton current flowing through the proton-conductive layer.

18. A CO-concentration measurement method which comprises:
introducing a gas under measurement into a first measurement space via a first diffusion-controlling section, and controlling hydrogen concentration in the first measurement space to a constant level by pumping hydrogen contained in the gas under measurement outside the first measurement space or pumping hydrogen into the first measurement space;
introducing into a second diffusion-controlling the gas under measurement present in the first measurement space having a controlled hydrogen concentration,
reacting CO contained in the gas under measurement with a hydrogen-containing substance at the second diffusion-controlling section to thereby generate hydrogen;
introducing into a second measurement space the gas under measurement present in the second diffusion-controlling section and containing the generated hydrogen; and
obtaining a CO concentration of the gas under measurement based on a concentration or amount if hydrogen in the second measurement space.

19. A CO-concentration measurement method which comprises:

introducing a gas under measurement into a first measurement space via a first diffusion-controlling section, and controlling hydrogen concentration in the first measurement chamber space to a constant level by pumping hydrogen containing in the gas under measurement outside the first measurement space or pumping hydrogen into the first measurement space;
introducing into a second measurement space, via a second diffusion-controlling section, the gas under measurement present in the first measurement space having a controlled hydrogen concentration;
reacting CO contained in the gas under measurement with a hydrogen-containing substance at the second measurement space to thereby generate hydrogen;
obtaining a CO concentration of the gas under measurement based on a concentration or amount of hydrogen in the second measurement space.

20. A CO-concentration measurement method which comprises:
providing a CO sensor which comprises a first measurement space in communication with a measurement gas atmosphere via a first diffusion-controlling section, a second measurement space in communication with the first measurement space via a second diffusion-controlling section, a first electrode disposed in contact with a first proton-conductive layer and located within the first measurement space, a second electrode disposed in contact with the first proton-conductor layer and located outside the first measurement space, a third electrode disposed in contact with a second proton-conductive layer and located within the second measurement space, a fourth electrode disposed in contact with the second proton-conductive layer and located outside the second measurement space, and a support for supporting the first diffusion-controlling section, the first measurement space, the second diffusion-controlling section, the second measurement space, the first proton-conductive layer, the second proton-conductive layer, the first electrode, the second electrode, the third electrode, and the fourth electrode,
introducing a gas under measurement into the first measurement space via the first diffusion-controlling section,
applying a first predetermined voltage between the first and second electrodes so as to control the hydrogen concentration within the first measurement space to a constant level by pumping hydrogen contained in the gas under measurement outside the first measurement space or by pumping hydrogen into the first measurement space,
introducing the gas selector measurement having a controlled hydrogen concentration from the first measurement space to the second measurement space via the second diffusion-controlling section,
reacting CO contained in the gas under measurement with a hydrogen-containing substance at the second diffusion-controlling section or at the second measurement space to thereby generate hydrogen,
dissociating the hydrogen gas produced by reactions of CO with the hydrogen-containing substance to thereby generate protons,
applying a second predetermined voltage between the third and forth electrodes so as to transport the protons thus generated through the second proton conductive layer, and measuring a limiting proton current flowing through the second proton-conductive layer to obtain the CO concentration of the gas under measurement.

21. A CO-concentration measurement method which comprises:

providing a CO sensor which comprises a first measurement space in communication with a measurement gas atmosphere via a that diffusion-controlling section, a second measurement space in communication on with the first measurement space via a second diffusion-controlling section, a first electrode disposed in contact with a first proton-conductive layer and located within the first measurement space, a second electrode disposed in contact with the first proton-conductive layer and located outside the first measurement space, a third electrode disposed in contact with a second proton-conductive layer and located within the second measurement space, a fourth electrode disposed in contact with the second proton-conductive layer and located outside the second measurement space, and a support for supporting the first diffusion-controlling section, the first measurement space, the second diffusion-controlling section, the second measurement space, the first proton-conductive layer, the second proton-conductive layer, the first electrode, the second electrode, the third electrode, and the fourth electrode, introducing a gas under measurement into the first measurement space via the first diffusion-controlling section, applying a first predetermined voltage between the first and second electrodes so as to control the hydrogen concentration within the first measurement space to a constant level by pumping hydrogen contained in the gas under measurement outside the first measurement space or by pumping hydrogen into the first measurement space, introducing the gas selector measurement having a controlled hydrogen concentration from the first measurement space to the second measurement space via the second diffusion-controlling section, reacting CO contained in the gas under measurement with a hydrogen-containing substance at the second diffusion-controlling section or at the second measurement space to thereby generate hydrogen, and measuring electromotive force generated between the third and fourth electrodes to obtain the CO concentration of the gas under measurement.

* * * * *